(12) United States Patent
Burdon et al.

(10) Patent No.: US 7,164,572 B1
(45) Date of Patent: Jan. 16, 2007

(54) MULTI-PATH, MONO-POLAR CO-FIRED HERMETIC ELECTRICAL FEEDTHROUGHS AND METHODS OF FABRICATION THERFOR

(75) Inventors: Jeremy W. Burdon, Minneapolis, MN (US); Joyce K. Yamamoto, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/227,523

(22) Filed: Sep. 15, 2005

(51) Int. Cl.
*H01G 4/35* (2006.01)

(52) U.S. Cl. ............... 361/302; 361/313; 361/321.2; 607/1; 607/5

(58) Field of Classification Search ............ 361/302, 361/306.1, 306.3, 311–313, 321.2, 303; 607/1, 607/5, 9; 29/25.41, 25.42
See application file for complete search history.

(56) References Cited

U.S. PATENT DOCUMENTS

| | | | | |
|---|---|---|---|---|
| 4,213,004 A | * | 7/1980 | Acker et al. | 174/151 |
| 5,905,627 A | * | 5/1999 | Brendel et al. | 361/302 |
| 6,567,259 B1 | * | 5/2003 | Stevenson et al. | 361/302 |
| 6,765,779 B1 | * | 7/2004 | Stevenson et al. | 361/302 |
| 6,888,715 B1 | * | 5/2005 | Stevenson et al. | 361/302 |

* cited by examiner

*Primary Examiner*—Anthony Dinkins
(74) *Attorney, Agent, or Firm*—Paul H. McDowall; Girma Wolde-Michael

(57) ABSTRACT

An electrical feedthrough assembly according to the invention can be used as a component of an implantable medical device (IMD) and/or or electrochemical cell. An IMD includes implantable pulse generators, cardioverter-defibrillators, physiologic sensors, drug-delivery systems, etc. Such assemblies require biocompatibility and resistance to degradation under applied bias current or voltage. In some forms of the invention, such assemblies are fabricated by using electrically common, multiply-interconnected electrical pathways including metallized vias and interlayer structures of conductive metallic material within bores and between ceramic layers. The layers are stacked together and sintered to form a substantially monolithic dielectric structure with at least one electrically common embedded metallization pathway extending through the structure. The metallization pathway reliably conducts electrical signals even when exposed to body fluids and tissue and providing electrical communication between internal IMD circuitry and active electrical components and/or circuitry coupled to the exterior of an IMD.

20 Claims, 13 Drawing Sheets

MULTI-PATH, MONO-POLAR CO-FIRED HERMETIC ELECTRICAL FEEDTHROUGHS AND METHODS OF FABRICATION THERFOR

CROSS REFERENCE TO RELATED APPLICATIONS

This patent disclosure is related to U.S. patent application Ser. No. 11/227,342 entitled, "IMPLANTABLE CO-FIRED ELECTRICAL FEEDTHROUGHS," U.S. patent application Ser. No. 11/227,375 entitled, "MINIATURIZED CO-FIRED ELECTRICAL INTERCONNECTS FOR IMPLANTABLE MEDICAL DEVICES," and U.S. patent application Ser. No. 11/227,341 entitled, "IMPLANTABLE CO-FIRED ELECTRICAL INTERCONNECT SYSTEMS AND DEVICES AND METHODS OF FABRICATION THEREFOR," each of which were filed on even date hereof and each of which is hereby incorporated by reference herein.

FIELD

The disclosure relates to improved miniaturized co-fire electrical interconnects and methods of manufacturing same for implantable medical devices.

BACKGROUND

Implantable medical devices (IMDs) are steadily being miniaturized and their functionality is increasing. This is driving size and cost reduction of all IMD components including the electrical feedthrough, where it is desirable to reduce device size while increasing the number of electrical feedthroughs and interconnects. Feedthroughs are required that operate in potted and unpotted conditions (requiring biocompatibility), and in addition the functionality of the implantable device often requires the device operate at a voltage-bias, which puts body fluid-contacting electrical connections under electrochemical stress which can possibly result in erroneous operation and/or device failure. In addition, there is a growing need to reduce the cost of the components used in medical devices. Current electrical feedthroughs are costly due to the many piece-parts and multiple processes required to fabricate and assemble these parts into a functional component.

For additional background on the general field of endeavor and context of the present invention, U.S. Pat. No. 6,743,534 issued to Lautzenhiser et al. on 1 Jun. 2004 and entitled, "Self-constrained low temperature glass-ceramic unfired tape for microelectronics and methods for making and using the same," is hereby incorporated by reference herein. An excerpt from the Background portion of the '534 patent follows to aid the reader in understanding certain aspects of the present invention as well as related and inherent aspects thereof.

The co-sintering or firing of laminated ceramic tapes is a well-known module manufacturing method in the microelectronics industry. The phrase low-temperature co-fired ceramic (LTCC) refers to a technology for forming multi-layered ceramic circuits. In this approach, a tape is formed from glass and ceramic powders uniformly dispersed in an organic binder. Typically, two or more layers of this tape are laminated together to form a circuit. To form electrical connections from one layer of tape to the next, via holes are punched through the tape and filled with a thick-film conductor paste, for example as described in U.S. Pat. No. 4,654,095 to Steinberg. In addition, other exemplary prior art includes U.S. Pat. No. 4,641,425 to Dubuisson et al. entitled, "Method of Making Alumina Interconnection Substrate for an Electronic Component" and U.S. Pat. No. 4,910,643 to Williams entitled, "Thick Film Multi-layer, Ceramic Interconnected Circuit Board." Further prior art also includes U.S. Pat. No. 4,464,420 to Taguchi et al. entitled, "Ceramic Multilayer Circuit Board and a Process for Manufacturing Same," U.S. Pat. No. 5,356,841 to Mitzutani et al. entitled, "Glass-Ceramic Composite" and U.S. Pat. No. 5,831,810 to Bird et al. entitled "Electronic Component Package with Decoupling Capacitors Completely within Die Receiving Cavity of a Substrate." The contents of these issued U.S. patents are hereby incorporated by reference herein.

Now continuing with reference to the '095 patent to Steinberg, in a next step, thick-film pastes (dispersions of metallic, ceramic or glass powders in volatilizable organic vehicles) that will form components of electronic circuits, such as conductors or resistors, are then screen-printed onto the tape. After all of the layers of tape necessary to form the completed circuit have been prepared, the pieces of tape are aligned to ensure that via connections from one layer will make contact with conductor traces or via holes on the next. The layers of tape are then laminated with a combination of heat and pressure to form a single green body, i.e., a structure that is held together by organic binders, such as polyvinyl butyral or acrylate materials. In order to form the final ceramic body, the green body is fired in a firing profile that typically reaches a peak temperature of about 850 degrees Celsius to 900 degrees Celsius before returning to ambient temperature. In a range of temperatures between about 350 degrees Celsius and 450 degrees Celsius, the organic binders that give the green body strength are volatilized or burned out. To give the volatilized gases sufficient time to escape, the ramp rate (change in temperature per unit time) of the profile is often reduced in this temperature range.

Above the burnout temperature, the ramp rate of the firing profile is increased and the part is heated until reaching the peak firing temperature. The LTCC tape typically contains a significant amount of a glass with which a glass softening point is associated. The glass and ceramic powders will begin to sinter into a dense body when the temperature is above the softening point of the LTCC glass, so the peak firing temperature of the tape is typically 100 degrees Celsius to 200 degrees Celsius above the glass softening point. The thick-film conductor and resistor materials used in the circuit body will undergo a similar metamorphosis from organically bound powders into dense sintered structures. After allowing the parts to remain at the peak firing time to reach an adequately dense body, the parts are cooled to room temperature.

Manufacturing of LTCC tapes is typically performed using tape casting techniques, such as those described in U.S. Pat. No. 5,821,181 of Ursula, et al. In this method, ceramic slurry (a mixture of the inorganic and organic components of the tape before drying) is deposited on top of a polyester film or carrier using a doctor blade. One disadvantage of using tape casting techniques for tape manufacturing is the difficulty of thickness control as the tape becomes thinner and thinner. More specifically, thickness, accuracy and variance become uncertain when casting under two mils (50 microns), a measurement which refers to the gap between the blade and the backing as the wet slurry passes through. Therefore, control of the layer thickness, especially of inner layers, becomes difficult and often inaccurate.

While accurate casting of individual layers is achievable, the method described in U.S. Pat. No. 5,102,720 for drying the tapes individually and subsequently laminating them together is uneconomical. Thus, methods which involve drying individual layers and lamination with heat and pressure, or casting a subsequent layer on top of a dry layer, not only introduce significant costs to the manufacturing process, but also limit product yields.

Other manufacturing methods include dipping a moving carrier film in a slurry to create a meniscus between the carrier film and the slurry. However, the meniscus created by capillary forces between the wet organic binder and the film causes it to stick to the surface of the polyester film. As in other methods, drying one layer at a time and then casting a wet layer on top of a dry layer or subsequent heat lamination are needed. Because of the disadvantages with known methods for manufacturing LTCC tapes, there remains a need in the art for an improved, economical method for fabricating LTCC tapes which will maximize product yield and permit tight control of layer thickness.

The LTCC technology has advanced beyond the microelectronic circuit industry and is currently in use for a variety of applications. One important attribute of LTCC is the ability to create three-dimensional structures using multiple layers of tape. The biomedical device industry, for example, uses LTCC for the manufacturing of cavities and channels for moving part pumps used in in-situ drug delivery systems. Biological test modules have been realized which facilitate the automatic testing of biological and chemical materials.

In the telecommunications industry, there is a need for integrated opto-electronic modules. LTCC offers the simplicity of being able to co-sinter optical fibers together with the driving electronics. The co-firing of meso-scale structures containing metallization, cavities, vias, and channels is thus an appealing feature of LTCC.

LTCC meso-systems are small packages capable of handling at least two media, such as electricity and fluids, by means of sensors, actuators, interconnection, control and/or signal processing. Miniaturization is one of the biggest drivers of this technology, thus allowing systems in package (SIP), in which several components are inserted into a monolith.

An attractive feature of LTCC tapes is the possibility for making cavities for the placement of integrated circuits within. For example, an electronic module can be fabricated that contains a cavity, a metallic via, and a metallic line trace on the surface of a ceramic monolith.

Cavities allow a module to retain a low profile, and according to certain prior approaches a lid can be placed on top for hermeticity. However, during surface or sacrificial constrained sintering, as explained below, the cavity walls exhibit a phenomenon called necking, a vertical curvature from the top surface interface to the bottom of the fired substrate surface. During sintering of sacrificially constrained structures, there is a stress distribution due to the shear and in-plane tensile stresses from top to bottom. It has been shown that stresses are significantly higher at the constrained interface. Moving along the z-axis towards the middle of the fired substrate, there are fewer constraining forces that counteract the in-plane tensile stresses. Therefore, there is significantly more densification in the middle of the monolith, which causes the vertical curvature. Furthermore, as a consequence of the higher stress distribution at the interface, delamination or buckling is usually present.

The aforementioned properties are undesirable, especially when constructing cavities or other precision features in the ceramic structures.

Despite the numerous applications of LTCC technology, the LTCC process has several disadvantages. First, there are significant changes in the dimensions of the ceramic monolithic structure during sintering. More specifically, when the constituent powders of the LTCC structure densify during traditional unconstrained or free sintering, shrinkage occurs in all dimensions. Typically, the shrinkage of the tape across its width or length (the x- or y-directions) will be nearly identical and only slightly different from the shrinkage through the thickness of stack-up of tape layers (the z-direction). Usually, the dimensions of the structure after firing will be about 84% to 87% of the size in the unfired green state. This change and the associated variations result in several disadvantages to the use of conventional LTCC technology that present challenges for the use of LTCC technology for certain applications (e.g., applications requiring a long-term hermetic seal, especially in the presence of corrosive fluids or the like).

During firing, the shrinkage uncertainty of the LTCC causes the external features to vary with respect to the intended nominal position. Artworks used for post-firing processes, such as the printing of post-fired conductors or resistors, or for printing solder on conductors, are based on the intended nominal position. Excessive distance between the actual fired position of a circuit feature and the nominal position can cause circuit failures if, for example, there is failure to make adequate electrical contact, which may result from lack of via connections or misalignments between layers due to non-uniform shrinkage. Alternatively, although artwork features may be enlarged to allow for such shrinkage variation, decreased circuit density may result.

Previously pressure-assisted sintering and the application of external loads to ceramic tape modules are described in U.S. Pat. No. 4,340,436. The use of mechanical clamping on the periphery of a ceramic panel to contain its x-y dimensions is also discussed in the prior art (see European Patent No. 0 243 858).

These types of approaches present several potential problems and disadvantages to the manufacturer. Because the presence of the platen may cause functional defects in any conductors or resistors which are in direct contact with the surface of the LTCC, the platen contact geometry must be carefully controlled and aligned with the green tape. Use of mechanical clamping techniques may require different platen designs for different circuits or geometry for an article fabricated using LTCC technology. Finally, a separate platen must be used for each constrained structure being fired in a batch.

Alternatively, the use of porous contact sheets attached to the LTCC panels that are easily removed after sintering is described in U.S. Pat. No. 6,139,666. Additionally, as described in U.S. Pat. No. 6,205,032 and U.S. Pat. No. 6,560,860 entitled, "Low Temperature Co-Fired Ceramic with Improved Registration," describes the use of a constraining ceramic core that constrains the attached layers using subsequent firings has been attempted.

A further technique for constraining the x-y geometry of LTCC circuits involves laminating sacrificial constraining tape layers onto the top and bottom surfaces of the LTCC circuit body. This technique has been described, for example, in U.S. Pat. Nos. 5,085,720; 5,254,191; 5,383,474; and 5,474,741, all by Mikeska, et al. The sacrificial tape layers are formed from porous, high temperature refractory ceramic powder that by itself will not sinter during the LTCC firing process. Since the sacrificial tape does not sinter and densify during the firing profile, it maintains the geometry of its green state.

However, in order for the sacrificial refractory tape to constrain the x-y geometry of underlying LTCC tape, at least two conditions should be met. First, there must be sufficient friction between the two tape materials to mechanically link the materials. Second, glassy components of the LTCC tape that could dissolve the refractory component of the sacrificial tape during the LTCC firing profile, thus allowing it to sinter and densify, must not saturate the sacrificial tape layer.

All of the aforementioned external constraint approaches have significant drawbacks. For example, pressure-assisted sintering and peripheral constraining require special adaptation of the furnace or the need for external equipment to mechanically prevent shrinkage of the ceramics. Other methods require the creation of refractory ceramic porous molds to form the tape for cavities.

Finally, several potential problems exist for manufacturers using sacrificial tape processes. After firing, the sacrificial tape layer must be removed from the circuit body sufficiently completely to not interfere with subsequent manufacturing processes, but not so aggressively as to damage the remaining LTCC body. Like the platen of the mechanical clamping technique, the sacrificial tape may be incompatible with conductors or resistors that may be placed on the surface of the LTCC circuit body. Therefore, these surface features must be printed and fired after removal of the sacrificial layer, which increases the number of processing steps on the manufacturing line and also results in increased cost of successive firings (furnace costs). From the standpoint of process yield and process simplicity, it would have been preferable to print these features on green tape and co-fire them with the rest of the circuit body. Further, because the sacrificial tape has virtually no mechanical strength after firing, it cannot be incorporated into the body of the LTCC circuit. This limits the thickness of bodies that can be constrained with this method, as the degree of constraint deteriorates with an increase in the distance from the constraining layer. Finally, contact sheets of refractory ceramic sacrificial tape have the potential for surface contamination of the LTCC tape, and the removal or dusting and waste of the sacrificial layer contribute to and reflect on the individual module cost.

SUMMARY

Unlike some prior art methods and apparatus, certain embodiments of the present invention involve use of low temperature co-fired ceramic (LTCC), high temperature co-fired ceramic (HTCC) and combinations of both LTCC and HTCC fabrication and processing methods and structures. In general, such ceramic structures are formed using particles of sinterable, inorganic oxides such as ceramics and glass-ceramics particles, and processed in layer form to allow integration of electrical conductors in the x, y and Z planes to form a substantially monolithic 3-dimensional integration circuit. In general, the inorganic oxides comprise a high-temperature dielectric such as alumina ($Al_2O_3$), Silica ($SiO_2$) or Zirconia ($ZrO_2$) or mixtures thereof, and glass suspended in an organic (polymer) binder. This material is derived from a precursor ceramic slurry, comprised of the various inorganic components dispersed in a mixture of polymer and solvent. This material is formed into thin-sheets using a 'tape casting process' utilizing a blade, a well-known and established process Individual sheets (or segments of tape) are printed with a metallized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metallized paste) vaporizes and/or is incinerated while the remaining material fuses or sinters. Typically materials suitable for use as cofireable conductors are Platinum, Iridium, Platinum-Iridium alloys, Silver, Gold, Palladium, Silver-Palladium or mixtures thereof, or Tungsten, Molybdenum and/or Moly-manganese or other suitable materials are typically constitute the metallized paste. Thus, the green sheets are patterned and then stacked and aligned in an appropriate laminated configuration. The stacked laminates are then fired at temperatures of about 600 to about 800 degrees Celsius (for LTCC) and about 1300 to about 1600 degrees Celsius (for HTCC). In most cases, the binder removal step is performed in an oxidizing atmosphere (air) to assure decomposition of the organic components. The subsequent sintering phases of the firing process may proceed in an oxidizing or inert atmosphere depending on the conductor system. For example, an LTCC that utilizes Gold or Gold-Palladium conductors or an Alumina HTCC system that uses Platinum will be fired in air, whereas a Tungsten-Molybdenum system will likely require an inert atmosphere such as $N_2/H_2$ mixture. In general, an LTCC system will employ a lower melting-point conductor metallization such as Gold or Silver, where HTCC technology typically employs high-melting point refractory metal pastes as conductors.

According to certain aspects of the present invention a family of low-cost, miniaturized, hermetic electrical feedthrough assemblies suitable for implantation within tissue and/or in direct or indirect contact with diverse body fluids is provided. Such miniaturized, hermetic electrical feedthrough assemblies are made by forming an electrical interconnect in one or more ceramic green-sheet layer(s), stacking and laminating the layers together, and sintering them together to form a substantially monolithic dielectric structure having at least one embedded metallization pathway extending through the structure. Said metallization pathway provides communication of electrical signals in a variety of medical applications, including those requiring voltage-bias. The assemblies hermetically seal to a portion of a housing of an IMD, for example, from internal circuitry to external circuitry and/or components and can be directly and/or indirectly exposed to living tissue and body fluids.

Herein from time to time the acronym MLC shall be used to indicate a multi-layer-ceramic comprised of HTCC- and LTCC-type materials. According to the invention, LTCC and HTCC technologies provide for reduced IMD volume and increased device density and functionality, and offering a low-cost route to part fabrication. According to the invention, LTCC and HTCC technologies enable the device to be processed in parallel in the green-state utilizing multiple ceramic green-sheet layers. Individual green-sheet layers are populated with electrical interconnects and can be inspected before assembly, greatly increasing yield. The HTCC fabrication process enables highly complex, hermetically-sealed electrical communication for an IMD with a single sintering step or, optionally, more than a single sintering step (according to LTCC and/or HTCC temperature regimes), and components for IMDs can be fabricated in large arrays further reducing component costs. The materials used for the HTCC fabrication of components and systems according to the invention (e.g., insulators, metallization paste) are selected for stability and biocompatibility with closely matched characteristics between the materials used, particularly when subjected to elevated temperature(s).

The feedthrough components according to the invention are uniquely adapted for hermetic insertion into enclosures for electrochemical cells configured for implantation in so-called active IMDs (e.g. primary and secondary batteries, capacitors, etc.), diverse implantable physiologic sensors or capsules for such sensors (e.g. pressure, temperature, electrogram, flow, pH, blood chemistry, impedance, saturated oxygen and surrogates therefor, etc.). To improve ease of conductive coupling to one or both of the opposing sides of a feedthrough constructed according to the invention, one or more bonding, or capture, pads can be affixed thereto. Such a capture pad can comprise a plate that is post-fired to bond to a surface via of a feedthrough or a volume of deposited electrically conductive powder of noble metals (e.g., platinum, iridium, Palladium, gold and alloys thereof) or refractory metals (e.g., niobium, tungsten, molybdenum, and alloys thereof) that are co-fired or post-fired during fabrication, deposited as a thin-film using most-any suitable thin-film deposition or plating technology. For example, physical vapor deposition, chemical vapor deposition, RF-sputtering techniques, DC-sputtering techniques, thermal spray techniques, electroplating and the like.

Optionally, an elongated conductor (e.g. a pin or ribbon, wire, or connector-block) can be coupled to a capture pad for connection to remote circuitry or components.

In addition, certain embodiments of the invention implement more than a single conductive path between opposing sides of a feedthrough assembly. For example, in the event that the conductive traces couple to a rapid high energy discharge circuit such as an implantable defibrillator a plurality of individual conductive pathways can be utilized to conduct the defibrillation waveform. Such a waveform can comprise a biphasic waveform having an amplitude on the order of several hundred volts. One advantage of this aspect of the invention relates to the fault tolerance two or more conductive paths provide. In addition to or in lieu of the foregoing, the size and/or shape of the metallized vias can be adjusted for an intended application. According to this aspect of the invention, one or more conductors intended to carry large amounts of electrical current can be designed with a larger diameter.

By the same token, in a multi-polar feedthrough structure for an implantable cardioverter-defibrillator (ICD), the very low power circuitry used for cardiac pacing can couple to relatively thin or smaller metallized vias while the very high power defibrillation therapy delivery circuits can couple to relatively large metallized vias. Also, one or more conductors coupled to very low power remote physiologic sensors or a telemetry antenna can couple to yet another size metallized via. A multi-polar feedthrough array can include a linear or non-linear array of capture plates or metallized vias. Of course, a multi-polar feedthrough can also implement a regular distribution, an irregular distribution, or a combination of regular and irregular distribution over the exposed surface of a co-fired ceramic feedthrough assembly.

The following table shows the bulk resistivity (ρ) of pure metals that may be employed for the invention:

| Metal | Bulk Resistivity (uOhm · cm) |
|---|---|
| Niobium | 16 |
| Platinum | 10 |
| Tungsten | 5.4 |
| Gold | 2.2 |
| Copper | 1.69 |
| Silver | 1.63 |

Referring now to equation X.

$$R_{eff} = \rho L/A \qquad \text{Equation X:}$$

Where $R_{eff}$ is the effective resistance of the structure, ρ is the bulk resistivity of the pure metal, L is the physical length of the conductor and A is the cross-sectional area of the conductor, it can be realized that although in general, the value for p for the cofired metallization is 10–100x lower than the pure metal, the reduction in length and/or the use of multiple conductor pathway allows Reff to be reduced. For example, where as in a conventional FT the pin conductor may be 8–20 mil, the cofire electrical FT may be as small as 2–10 mil. In addition, multiple cofire FT vias may be electrically connected in parallel to drastically reduce the effective resistance, while still maintaining the desired lower profile. This concept of using multiple vias in illustrated in FIG. 13, which depicts the external to internal to external co-fire FT architecture, utilizing three dielectric layers (with alternating three-via arrangement), two circular interconnect pads to interconnect the three-via electrical interconnects internally, and two external interconnect pads (top and bottom of the device).

In terms of the shape of a metallized via and/or a capture plate affixed to a via in order to enhance accuracy of automated and manual assembly a via or capture plate can be designed with a recognizable characteristic shape, size, color and/or the like so that, particularly for multi-polar feedthrough assemblies, the ultimate electrical couplings are accurately and reliably secured with the aid or human- or machine-vision assisted pick and place component assembly equipment.

With respect to hermeticity, testing of a plurality of three layer cofired feedthrough units revealed that approximately 30 pounds of force was required to produce dislodgement of feedthroughs that were brazed using an annular gold perform or diffusion-bonded using thin-film Niobium interlayer, into a titanium ferrule fitted into an aperture formed in a titanium plate. In fact this force exceeded the tensile strength of the co-fire ceramic insulator, as the device always fractured within the ceramic, not at the ceramic-ferrule interface. In addition, during leak testing such units were immersed in a saline solution maintained at approximately 37 degrees Celsius (approximate body temperature) and approximately 95 degrees Celsius for thirty days both with an applied nominal bias voltage (2.2 V, 4.0 V) and without any bias voltage and no leakage was detected. The foregoing testing was performed on unipolar feedthrough units comprising three ceramic layers and two interlayers of a platinum paste co-fired at approximately 1550 degrees Celsius for approximately four hours. Note that while Au-brazing or diffusion-bonding was utilized other suitable bonding techniques can be used such as RMB (reactive metal brazing) and the like.

Structures according to the invention can be aligned using fiducial marks, laser or other optical mechanisms or the like. Typically the lateral side wall portions of a feedthrough according to the invention are aligned substantially parallel to adjacent and opposing side wall portions; however, the side wall portions can be fabricated at any reasonable angle relative to adjoining structure(s) and/or can be fabricated with a varying topography. In addition to or in lieu of such fabrication, one or more surfaces of a co-fired structure can be mechanically altered prior to or subsequent to one or more sintering steps. Cofire devices will typically be singulated from a larger array multilayer ceramic wafer. A variety of singulation methods are useful to define the geometry of the feedthrough and define the geometric and physical nature of the surfaces of the device. Devices may be singulated in the pre-sintered, or 'green' state, or subsequent to sintering. A variety of methods may be used, including, but not limited to 'green-dicing', laser-cutting, wafer-dicing diamond-saw, wafer-knife, or laser-assisted water-jet. Furthermore, a feedthrough according to the invention can be surrounded or embedded in a suitable potting compound, coated and/or other materials can be applied to one or more surfaces of the structure. This adds to the mechanical and fluidic stability of the device.

The following drawings depict several exemplary embodiments of the invention and are not intended as limiting but rather illustrative of certain aspects of the invention. The drawings are not drawn to scale and common reference numerals are used to denote similar elements of the invention.

DETAILED DESCRIPTION OF THE ILLUSTRATED EMBODIMENTS

Figure 1:
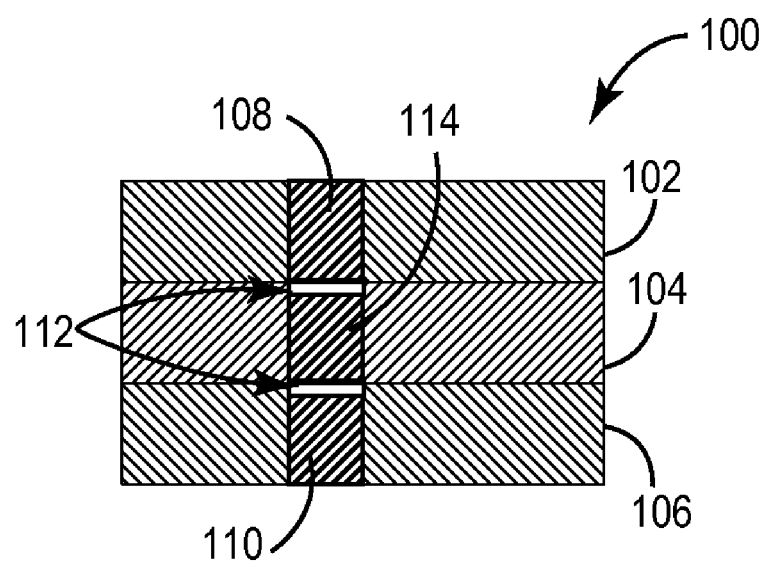
FIG. 1 depicts an elevational side view in cross-section of a hermetic electrical interconnect fabricated using three discrete layers of ceramic co-fired to form a monolithic structure with a straight via structure forming a continuous electrical pathway through the substrate.

The following discussion is presented to enable a person skilled in the art to make and use the embodiments of the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives, which fall, within the scope of the invention.

FIG. 1 depicts an elevational side view in cross-section of a hermetic electrical interconnect assembly 100 fabricated using three discrete green-state layers 102, 104, 106 of ceramic co-fired to form a monolithic structure with a substantially linear via structure 108, 110, 114 which when filled with a conductive paste (e.g., a platinum, platinum-gold, platinum-iridium or other refractory metallic, metallic alloy paste, silver, silver-palladium, gold, gold-palladium or mixtures thereof, tungsten, tungsten-molybdenum, niobium or other refractory metal system) forms a continuous electrical pathway through the layered substrate 102, 104, 106. A pair of conductive interlayers 112 are optionally disposed in between opposing via structures. In the depicted embodiment the interlayers 112 have approximately the same dimension as the corresponding via structure, although different dimensions can be utilized. The interlayer can be formed of the same conductive paste material that is used to fill the via structure 108, 110, 114 or other conductive material. While the embodiment depicted in FIG. 1 forms a hermetically sealed electrical substantially linear pathway through the structure 100, the possibility exists that when subjected to body fluids for an extended period of time the linear pathway might allow for fluid ingress. By meandering the interconnect using a staggered via geometry, additional internal ceramic-metal interface pathway is introduced, resulting in an extended diffusion-distance.

Figure 2:
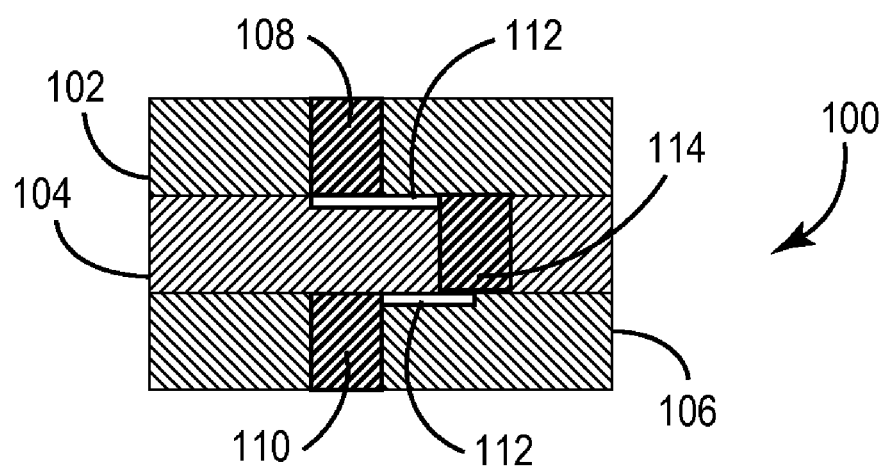
FIG. 2 depicts an elevational side view in cross-section of a three-layer hermetic electrical interconnect fabricated using three discrete layers of ceramic co-fired to form a monolithic structure with a staggered via structure forming an electrical pathway through the substrate.

Turning now to FIG. 2 an elevational side view in cross-section is presented for a three-layer hermetic electrical interconnect 100 fabricated using three ceramic green-sheet layers co-fired to form a monolithic structure with a staggered via structure 108, 110, 114 (and interlayers 112) forming a serpentine electrical pathway through the substrate layers 102, 104, 106. The depicted embodiment illustrates a variety configuration for interlayer 112 which can include substantially complete coverage for one of the metallized vias (108), abutting a metallized via (110), and partially covering a metallized via (114). The staggered configuration for the metallized vias 108, 112, 114 enhance the hermeticity of the structure 100 as well as increasing the resistance to fluid ingress through the structure 100.

Figure 3:
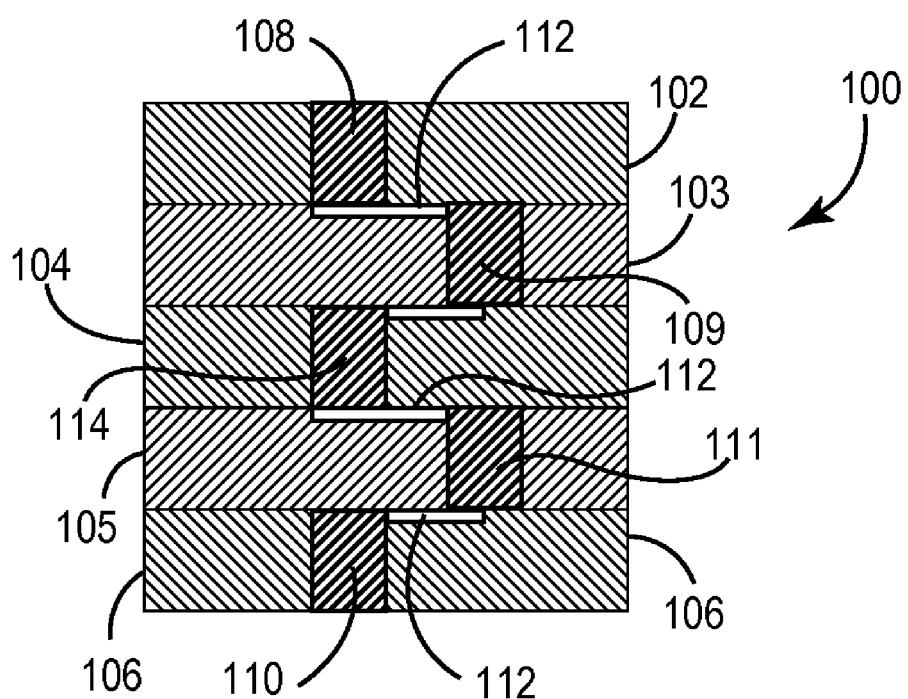
FIG. 3 depicts an elevational side view in cross-section of a five-layer hermetic electrical interconnect which is fabricated of five layers of ceramic green-sheet co-fired to form a monolithic structure with a staggered via structure forming a continuous electrical pathway through the fired substrate.

An embodiment related to the one depicted in FIG. 2 is shown in FIG. 3. Wherein FIG. 3 depicts an elevational side view in cross-section of a five-layer hermetic electrical interconnect 100 which is fabricated of five layers of ceramic green-sheet 102–106 co-fired to form a monolithic structure with a more complex serpentine via structure forming a continuous electrical pathway through the fired five layer substrate 100. The optional interlayers 112 depicted in FIG. 3 illustrate that they can completely or partially overlap an adjacent metallized via and/or can abut a side portion of a metallized via to establish electrical communication therethrough.

Figure 4:
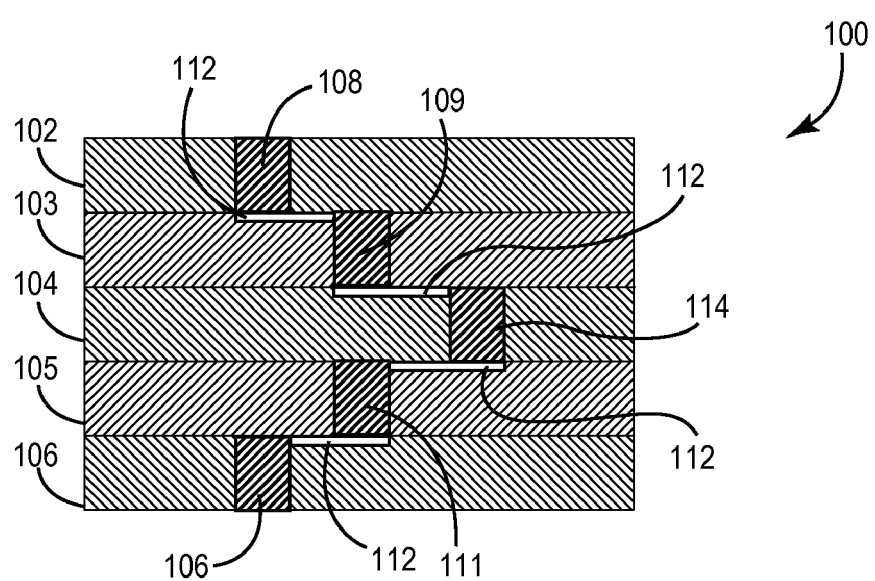
FIG. 4 depicts an elevational side view in cross-section of a five-layer hermetic electrical interconnect fabricated of five layers of ceramic green-sheet co-fired to form a monolithic structure with an alternate staggered via structure forming an operative electrical pathway therethrough.

FIG. 4 depicts an elevational side view in cross-section of a five-layer hermetic electrical interconnect 100 fabricated of five layers of ceramic green-sheet 102–106 co-fired to form a monolithic structure with a staggered via structure 108–111, 114 (and including optional interlayers 112) forming an operative electrical pathway through the interconnect 100.

Figure 5:
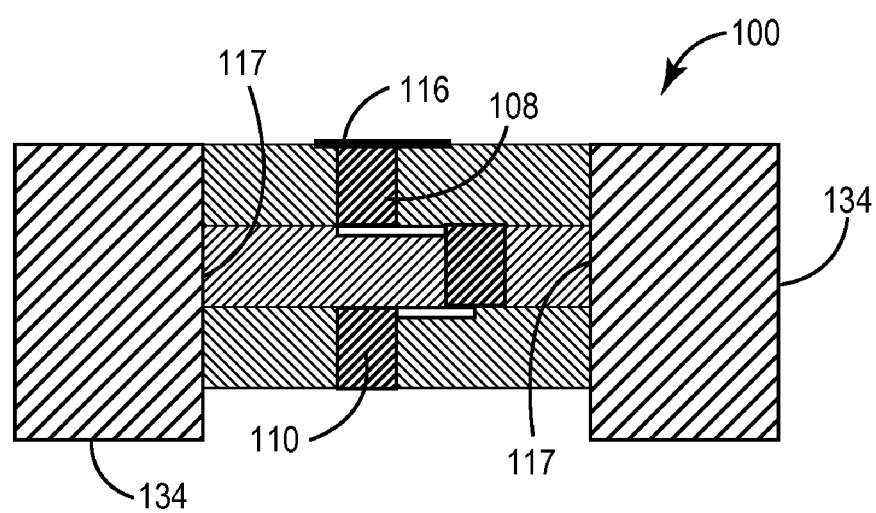
FIG. 5 depicts an elevational side view in cross-section of a three-layer hermetic electrical interconnect which includes a surface electrical connection pad.

FIG. 5 depicts an elevational side view in cross-section of a three-layer hermetic electrical interconnect 100 which includes a surface electrical connection pad, or capture pad 116. In FIG. 5 a schematic representation of a ferrule 134 is depicted that surrounds the lateral side wall 117 of the interconnect 100. The capture pad 116 can be co- or post-fired and can comprise a metallic powder or paste with the finally processed material formed into a sintered metal film or plate. The capture pad 116 can be configured into any convenient shape, thickness, color or the like to promote accurate automated and/or manual connection to remote circuitry or components. The capture pad 116 can extend near, toward or to the periphery of the interconnect assembly 100; however, so-called fringe effects might inhibit performance of the assembly, particularly if one or more of the conductive paths include capacitive filtering components or the like. In the event that a metallic ferrule 134 surrounds the lateral side walls of the interconnect 100, then the capture pad 116 should be designed to decrease any likelihood of direct electrical contact or arcing between the ferrule and the capture pad 116 so that short circuiting is avoided.

In the embodiments depicted in FIGS. 1–5 the final or exposed metallized vias 108, 110 are aligned with each other. Of course, depending on the application and desired spacing and presence of other conductive pathways these exposed vias 108, 110 can be spaced apart in an x-y reference plane defined by the exposed surfaces.

Figure 6:
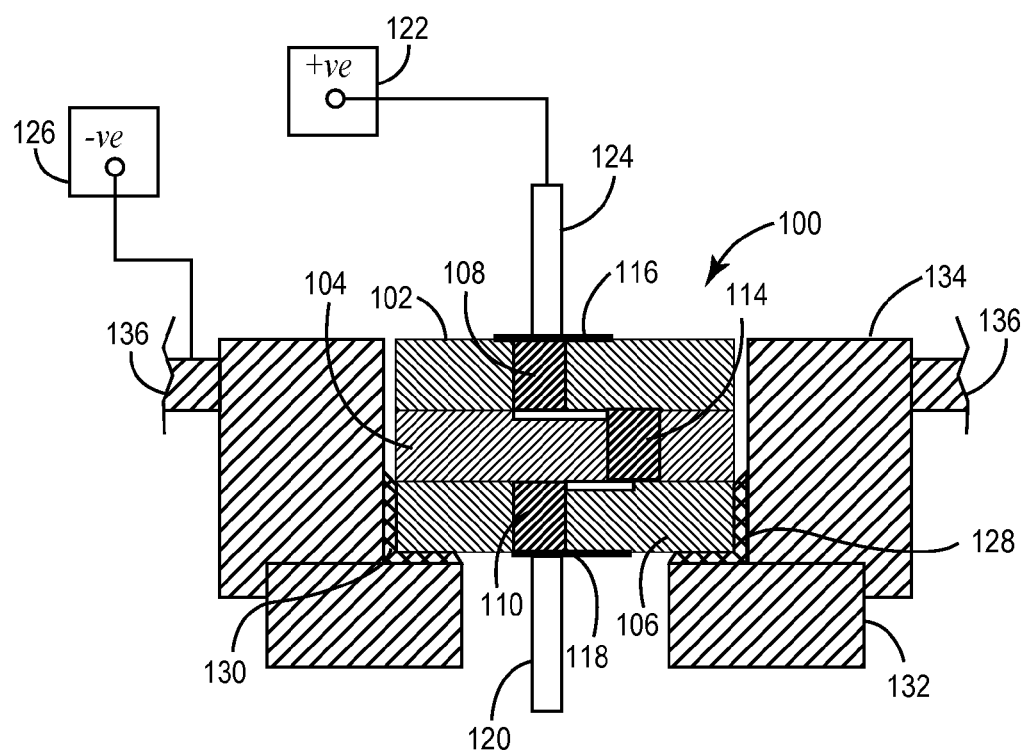
FIG. 6 depicts an elevational side view in cross-section of a hermetic electrical interconnect fabricated using three-layers of ceramic green-sheet co-fired to form a monolithic structure with a staggered via structure coupled to a metallic ferrule structure.

A gold (Au) braze stop and a weld-flange are also depicted and further increase the hermeticity of the feedthrough as depicted in FIG. 6, which is an elevational side view in cross-section of a hermetic electrical interconnect 100 fabricated using three-layers of ceramic green-sheet 102, 104, 106 co-fired to form a monolithic structure with a staggered via structure 108, 110, 114 coupled to a ferrule structure 134. The ferrule 134 is sized to receive the interconnect 100 can comprise a metallic member although it can be fabricated of any suitable material including resin and the like. In the event that metal is used to fabricate the ferrule 134 an optional dielectric coating (e.g. oxide or polymer material) can be added to one or more exposed surfaces of the ferrule 134. As depicted in FIG. 6 an optional lower support member 132 couples to ferrule 134. Of course, the member 132 can be integrally formed with the ferrule 134 and can be fabricated of a wide variety of materials. Between the ferrule 134, member 132 and the interconnect 100 resides a bonding material 128, 130. In practice the material 128, 130 typically consists of a single material continuously disposed around the periphery of the interconnect 100. In one embodiment the material 128, 130 comprises a gold-based braze material but it could also consist of a diffusion bond or the like. If any open space exists between the material 128, 130, the ferrule 132 and the interconnect 100 then an optional potting compound (not shown) can be applied that will protect the material 128, 130 from direct contact from corrosive body fluid or the like.

Also depicted in FIG. 6 is an edge portion of a sheet of material 136. The material 136 comprises a portion of an enclosure for an IMD, a sensor, an electrochemical cell or other article or component which requires electrical communication. In some forms of the invention the material can comprise titanium, titanium alloys, tantalum, stainless steel, or other metals. Capture pads 116, 118 are coupled to the final metallized vias 108, 110 and optional elongated conductors 124, 120 respectively couple to the pads 116, 118. A number of interconnect technologies are useful for providing robust electrical connections to pads 116,118, providing extended electrical connections 120, 124. These technologies include, but are not limited to, parallel-gap-welding (PGW), resistance-spot-welding (RSW), ultrasonic (wire)

bonding, thermosonic bonding, laser-ribbon-bonding (LRB). Or course the type and geometry of the interconnect need not be limited to that depicted in 120, 124. Additional type and geometries may include wire, ribbon, pin, or connector block, and the like.

A source of electrical energy 122 couples to conductor 124 and a relative electrical reference or ground couples to the material 136. In operation the energy source 122 couples to circuitry or components disposed within the enclosure 136 and the circuitry couples to the reference 126.

Figure 7:
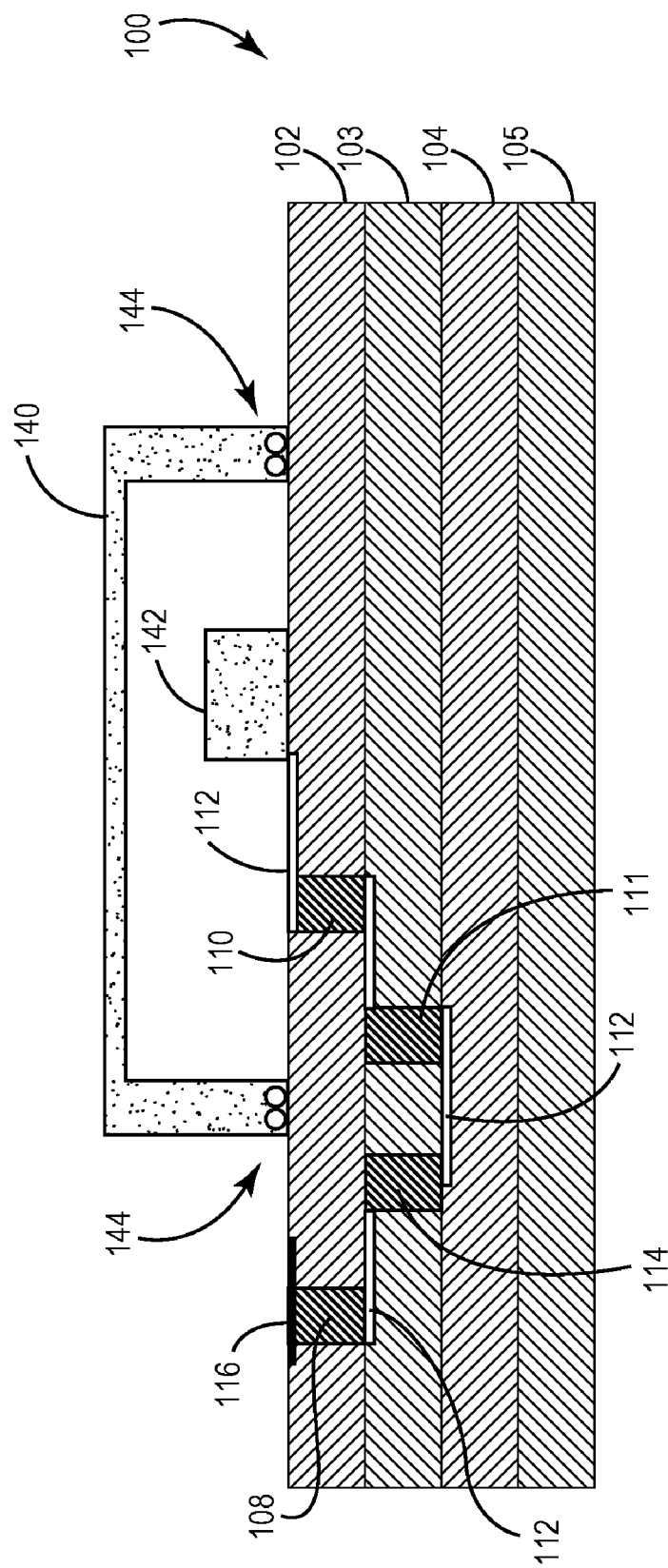
FIG. 7 depicts an elevational side view in cross-section of a hermetic electrical interconnect fabricated using four-layers of ceramic green-sheet co-fired to form a monolithic structure with a staggered via structure forming an electrical pathway from within a hermetically-sealed portion of an electrical device (housing) to an external location of the device.

FIG. 7 depicts another embodiment of the invention in an elevational side view in cross-section of a hermetic electrical interconnect 100 fabricated using four-layers of ceramic green-sheet 102–105. The layers are co-fired to form a monolithic structure with a staggered via structure 108, 110, 111, 114 which in combination with a plurality of interlayers 112 forms an electrical pathway from circuitry or components 142 disposed within a hermetically-sealed portion of an electrical device enclosure 140 to an external location of the device (at capture pad 116). In the depicted embodiment the interconnect 100 serves as a cover for the enclosure 140 and is physically coupled to the periphery of the enclosure 140 with a suitable bond 144. Such a suitable bond can be formed by laser welding techniques or alternatively by diffusion bonding. In FIG. 7 the circuitry or components 142 couple directly to a surface mounted interlayer 112 but could be coupled directly to metallized via 110.

Figure 8:
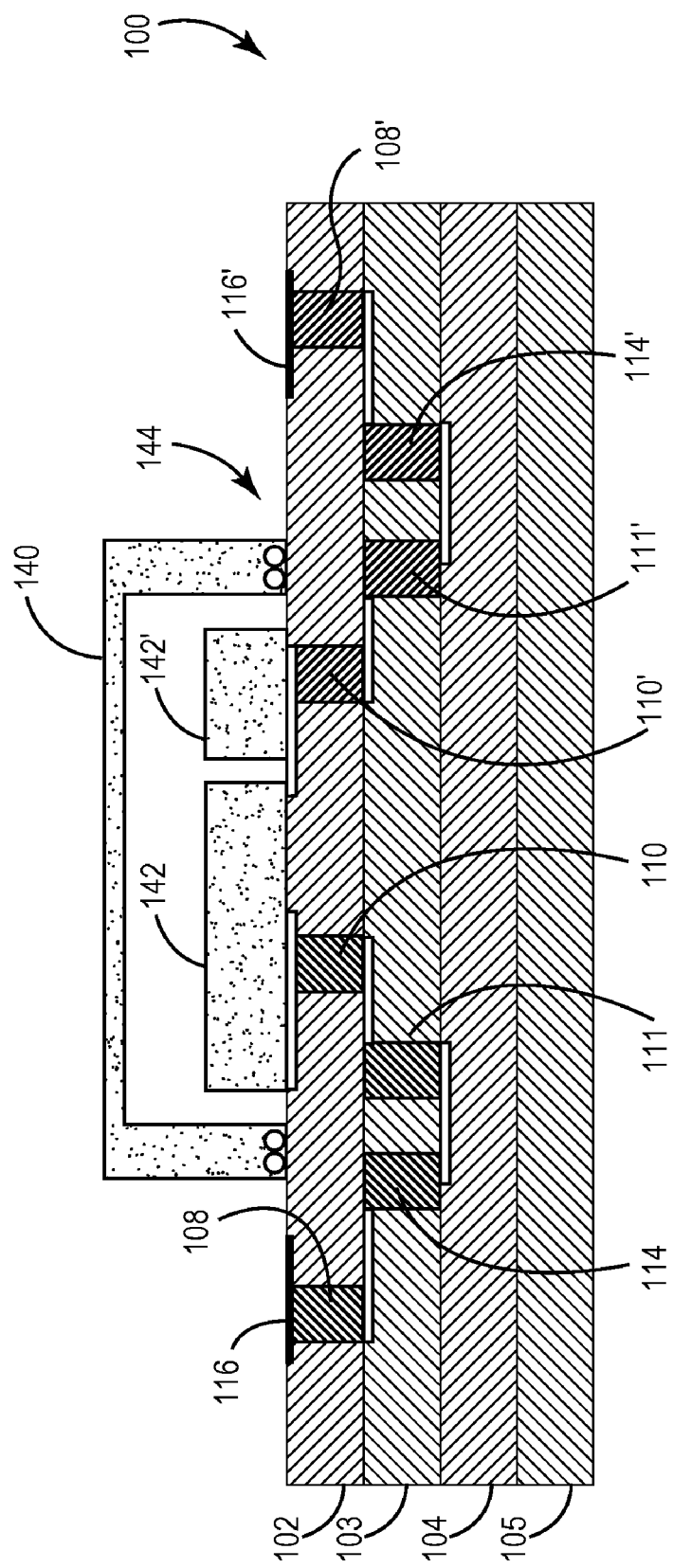
FIG. 8 depicts an elevational side view in cross-section of a hermetic electrical interconnect fabricated using four-layers of ceramic green-sheet co-fired to form a monolithic structure with a staggered via structure forming an electrical pathway from within a hermetically-sealed portion of an electrical device (package) to different locations external to the device.

FIG. 8 illustrates an embodiment of the invention related to the embodiment depicted in FIG. 7. That is, FIG. 8 depicts an elevational side view in cross-section of a hermetic electrical interconnect 100 fabricated using four-layers of ceramic green-sheet 102–105. The layers are configured to form a co-fired monolithic structure with a pair of staggered interconnected via structures 108, 110, 111, 114 (with the second set of structured denoted as prime numerals of the first set) forming a pair of individual electrical pathways including the plurality of interlayers (not numbered). The pathways extend from circuits and/or components 142, 142' commonly disposed within a hermetically-sealed portion of an electrical device (package) 140 to spaced apart locations external to the device (capture plates 116). Of course, the circuits and/or components 142, 142' can reside within a single hermetically sealed enclosure (as depicted, 140) of within two or more such enclosures (not depicted). Although the schematic depiction of FIG. 8 shows a relatively large interconnect 100 as compared to the enclosure 140 in practice typically the opposite it true. In fact, at least with respect to IMDs, the interconnect 100 can hermetically seal to a small aperture formed in one of a pair of metallic (e.g. titanium) shield halves.

Figure 9:
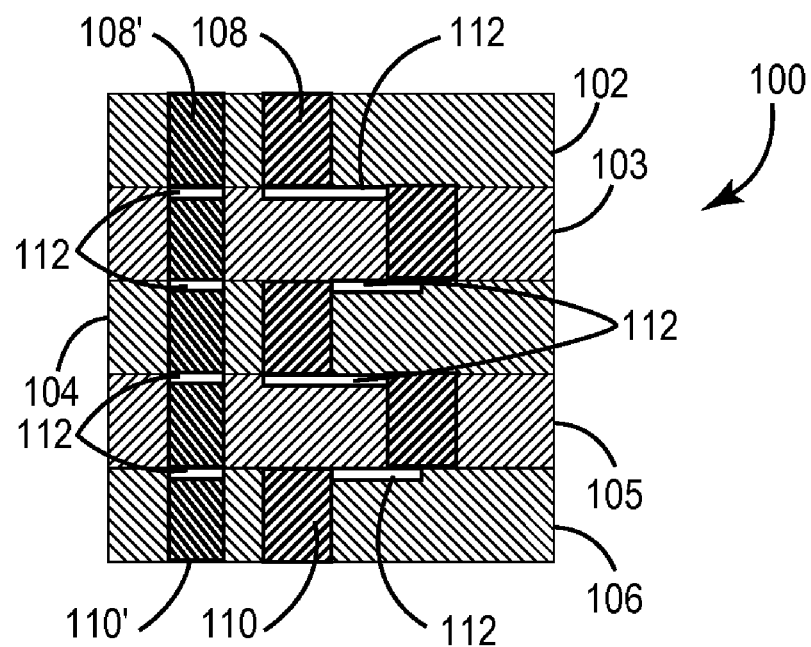
FIG. 9 depicts an elevational side view in cross-section of a hermetic electrical interconnect fabricated using five discrete green-state layers of ceramic co-fired to form a monolithic structure with a substantially straight via structure forming a first continuous electrical pathway through the substrate and a second conductive path composed of a staggered via structure forming a second electrical pathway through the laminated feedthrough structure.

FIG. 9 depicts an elevational side view in cross-section of a hermetic electrical interconnect 100 fabricated using five discrete green-state layers of ceramic 102–106 co-fired to form a monolithic structure with a substantially straight via structure forming a first continuous electrical pathway between metallized via 108' and 110' and a second conductive path (composed of a staggered via structure) between metallized via 108 and 110) forming a second electrical pathway through the laminated feedthrough structure 100. As depicted, the first and second pathways includes optional interlayers 112 between adjacent metallized vias. In FIG. 9 the first pathway appears to have metallized vias of similar cross section, or size, as the second pathway. However, the dimensions of the electrical pathways can be independently configured for a given application. As previously described and as will be depicted in FIGS. 11A–11C, both the type(s) of metallic paste used to fabricate an interconnect 100 according to the invention and the cross sectional size (and/or shape and color) of a given via can be determined on a case-by-case basis. For example, a high energy electrical pathway can have a relatively larger cross section dimension and/or multiple discrete pathways through the interconnect 100 or said pathways can be distributed through more than one interconnect 100.

Figure 10:
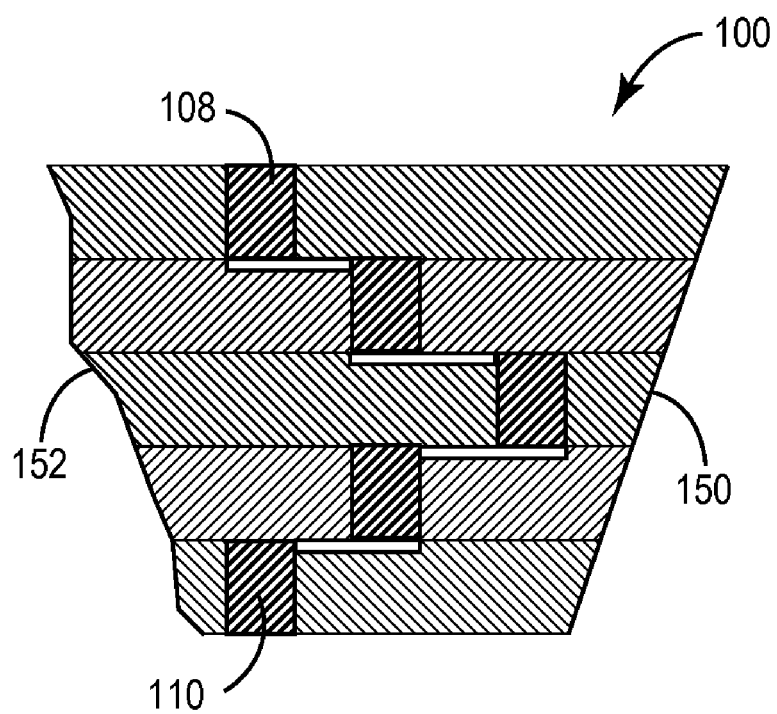
FIG. 10 depicts an elevational side view in cross-section of a five-layer hermetic electrical interconnect having a first side portion angled relative to the upper and lower end surfaces and a second side portion having an irregular surface topography.

FIG. 10 depicts an elevational side view in cross-section of a five-layer hermetic electrical interconnect 100 having a first side portion 150 substantially consistently diverging relative to the upper end surface (wherein metallized via 108 is disposed) and a second side portion 152 having an irregular surface topography. The side portions 150, 152 can be configured to enhance fixation of the interconnect 100 within an aperture and the configuration can be obtained prior or subsequent to a co-firing (and/or post-firing) sequence. In addition, the side portions 150, 152 can be obtained manually or with aid of precision machining systems (e.g. a computer numeric controlled or CNC mill or the like).

Figure 11A:
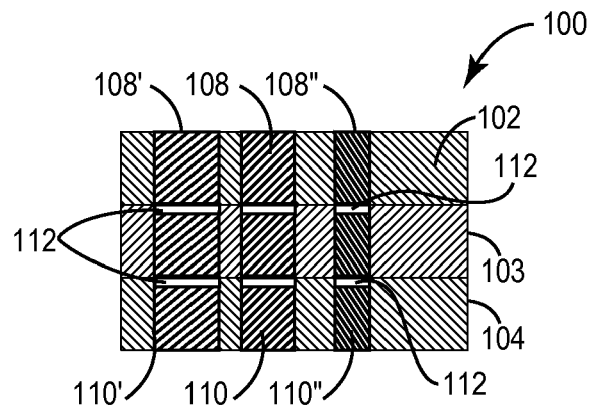
FIG. 11A depicts an elevational side view in cross-section of a hermetic multi-polar electrical feedthrough fabricated using three discrete green-state layers of ceramic co-fired to form a monolithic structure with three dissimilar, substantially straight via structures forming first, second and third continuous electrical pathways through the laminated structure.

FIG. 11A depicts an elevational side view in cross-section of a hermetic multi-polar electrical feedthrough 100 fabricated using three discrete green-state layers of ceramic 102, 104, 106 co-fired to form a monolithic structure with three dissimilar, substantially straight via structures forming first, second and third continuous electrical pathways through the laminated structure. As depicted, the first pathway lies between metallized vias 108 and 110, the second pathway lies between vias 108' and 110', and the third pathway lies between vias 108" and 110". The third pathway includes three similarly sized metallized vias with interlayers 112 disposed between adjacent vias. FIG. 11A illustrates a configuration wherein each electrical pathway differs in cross section dimension. For example the first pathway could carry an intermediate electrical load as between a pair of cardiac pacing electrodes while the second pathway carries a heavy electrical load as between a pair of defibrillation electrodes. The third pathway could carry a low or an ultra-low power electrical load such a signal from a chronically implanted physiologic sensor or the like (e.g. pressure, temperature, electrogram, flow, pH, blood chemistry, impedance, saturated oxygen and surrogates therefor, etc.).

Figure 11B:
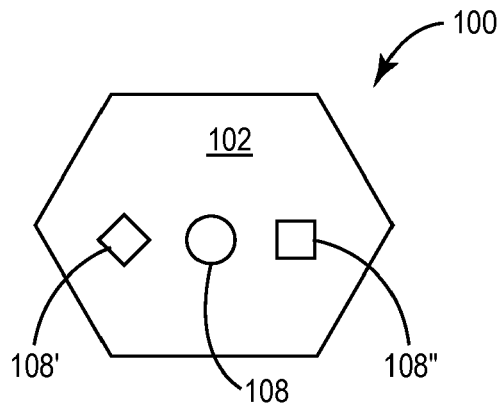
FIG. 11B depicts a plan view of the laminated structure depicted in FIG. 11A and illustrates an exemplary irregular geometric shape of the upper surface thereof in addition to a variety of sizes and shapes of the upper surface of the linear array of the metallized vias (and/or capture plates) of the multi-polar electrical feedthrough.

FIG. 11B depicts a plan view of the laminated interconnect structure 100 depicted in FIG. 11A and illustrates an exemplary irregular geometric shape of the upper surface thereof (layer 102). That is, the plan view of the periphery of layer 102 illustrates an irregular geometric shape (i.e. a hexagon). In addition, as noted with respect to FIG. 10, one or more side wall portions of the interconnect 100 can vary in topography. The periphery of layer 102 can be configured with regular and/or irregular features including linear and/or having constant or changing radius dimensions for any corner or fiducial features.

In addition to the shape of the upper (and other) layer 102 the size, shape and/or color of the exposed metallized vias can vary according to the invention. In FIG. 11B, the via 108 includes a substantially round upper surface. Via 108' includes a substantially rectangular-diamond upper surface and via 108" includes a substantially square upper surface. A wide variety of sizes and shapes of the upper surface of the linear array of the metallized vias 108, 108', 108" (and/or optional capture plates) of the multi-polar electrical feedthrough 100 thus expressly lie within the scope of the present invention.

Figure 11C:
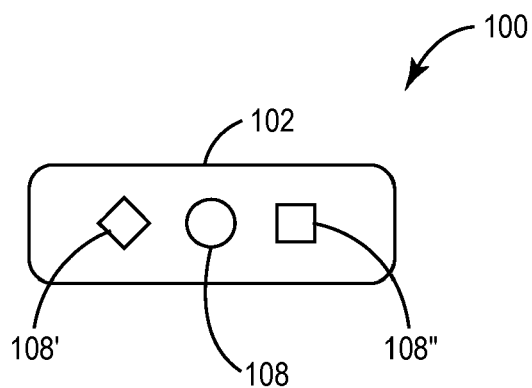
FIG. 11C depicts a plan view of an alternate configuration for the multi-polar feedthrough depicted in FIG. 11A and illustrates an exemplary linear array arranged upon the upper surface thereof as well as the variety of sizes and shapes of the upper surface of the metallized vias (and/or capture plates) of the multi-polar electrical feedthrough.

FIG. 11C depicts a plan view of an alternate configuration for the multi-polar feedthrough 100 depicted in FIG. 11A and illustrates an exemplary linear array of vias 108, 108', 108″ arranged upon the upper surface layer 102 as well as the variety of sizes and shapes of the upper surface of the metallized vias (and/or capture plates) of the multi-polar electrical feedthrough 100.

Figure 12:
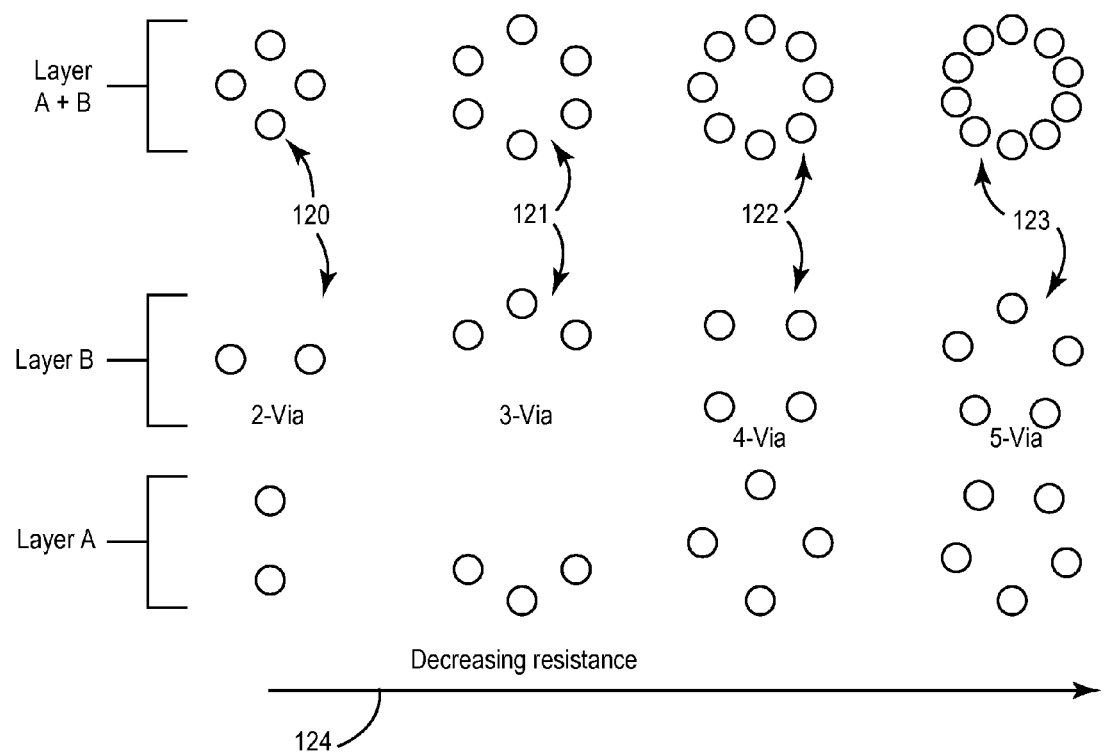
FIG. 12 depicts a schematic view of four discrete configurations for 2-via, 3-via, 4-via and 5-via structures wherein the via structures of a given layer of green-state material are offset from the adjacent via structures; also depicted is that relative impedance decreases from the 2-via to the 5-via configuration.

FIG. 12 depicts a schematic view of four discrete configurations for 2-via, 3-via, 4-via and 5-via structures 120–123 wherein the via structures of a given layer of green-state or a co-fired material layer (not shown but denoted by brackets labeled Layer A and Layer B) are offset from adjacent via structures of abutting layers. In addition, a plan view of the via structures 120–123 when Layer A and Layer B are aligned is depicted at the upper portion of FIG. 12.

Also depicted in FIG. 12 is the relationship between resistance or impedance from the 2-via to the 5-via configuration (decreasing as illustrated by arrow 124). For example, at 120 the 2-via structures of Layer A are aligned in a first orientation while the 2-via structures of Layer B are aligned in an second orientation offset from the first orientation. In certain embodiments the first and second orientation can be offset approximately 90 degrees, but other offset configurations are expressly within the purview of the instant invention. An internal interconnecting layer and/or a surface capture pad (not depicted) can be utilized to electrically couple the four discrete via structures together to increase redundancy and improve the signal carrying capacity of a 2-via structure versus a single via structure. The offset orientation also reduces the likelihood of tolerance stack wherein if the via structure are axially aligned, a slight deformation or rise in the surface of the interconnect can occur.

Now turning to the 3-via structure 121 wherein the triple via structures of a given layer of green-state or a co-fired material layer—again denoted by brackets labeled Layer A and Layer B—are offset from adjacent triple via structures of abutting layers. The inventors discovered that a greater relative improvement in performance (e.g., decreased electrical resistance and signal-carrying efficiency) was empirically shown from the 2-via structure to a 3-via structure.

In the depicted embodiment at the upper portion of FIG. 12, it is apparent that when Layer A is aligned with Layer B then the via structures are relatively evenly dispersed in an orderly geometric pattern. Although such a pattern is depicted in FIG. 12, the instant invention is not to be limited to such patterns. In fact, the offset orientation of the via structures can be disposed in any convenient or desirable configuration including regular and irregular as well as with different cross-sectional areas (as previously described) and individual via structure shapes.

With respect to the 4- and 5-via structures depicted in FIG. 12, similar aspects as just described are apparent to one of skill in the art. In addition, although only a pair of layers are schematically depicted (i.e., Layer A and Layer B), no such limitation should be ascribed to the invention; in fact multiple-layer hermetic interconnect structures are fully within the scope of the instant invention.

Also, while not specifically depicted the invention also includes multiple layer interconnect structures having different number(s) of via structures commonly electrically coupled together. For instance, one or more layers could have a 3-via or 4-via structure while other layers have a 2-via or 6-via structure co-fired therein and interconnected.

Figure 13:
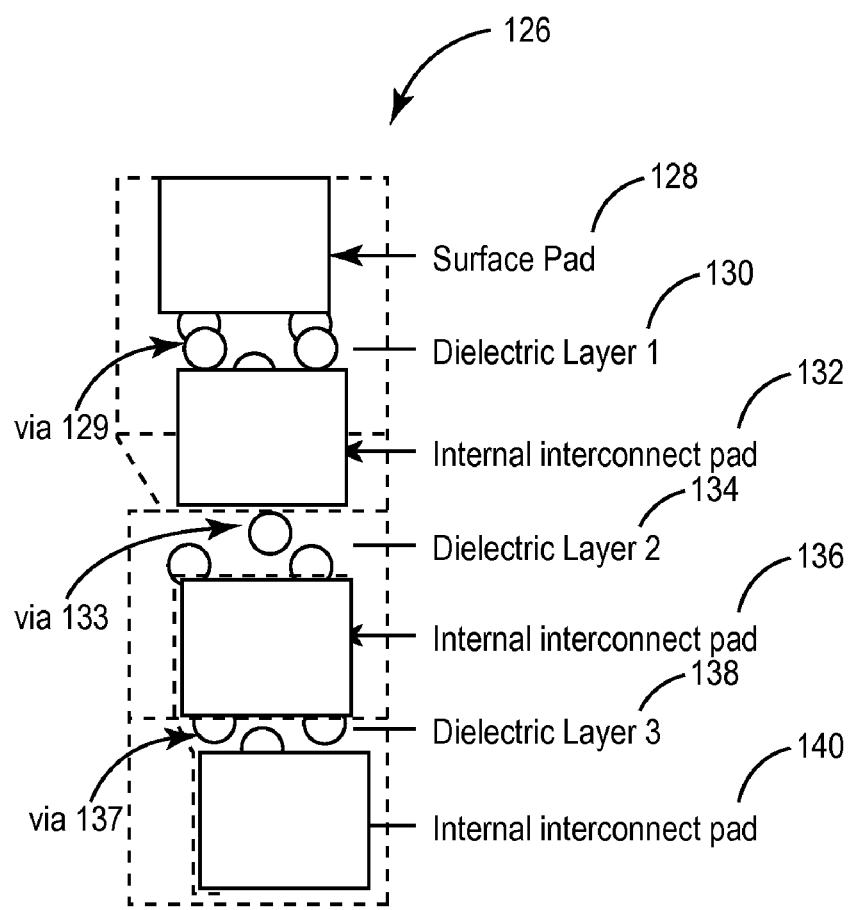
FIG. 13 is a perspective view of the relative location and size of internal interconnect pads, surface capture pad, and via structures (with the dielectric layers not depicted).

FIG. 13 is a perspective view of the relative location and size of internal interconnect pads 132, 136, 140 a surface capture pad 128, and via structures 129, 133, 137 with the dielectric layers 130, 134, 138 (depicted in ghost). FIG. 13 illustrates one embodiment of a common electrical coupling of offset multiple via structures disposed in each dielectric layer 130, 134, 138 using a plurality of interconnect pads 132, 136, 140. Although the interconnect pads are intended to show that each pad couples to all via structures of adjacent layers, more than one interconnect pad can be used to conduct signals through a given layer or layers of a hermetic interconnect structure according to the invention.

In some embodiments of the invention, an interconnect 100 functionally couples to the periphery of a receiving aperture or port using brazing techniques. Brazing involves joining two discrete parts by fusing a layer of a brazing material (e.g. a metal such as gold) between adjoining surfaces of the parts. Generally, the process involves a braze melting and flowing between the two parts, commonly referred to as wetting. The braze material may form an interlayer that provides a suitable thermochemical and hermetic seals between the joined parts. In some embodiments, the parts are coupled using reactive metal brazing (RMB) techniques. Such RMB techniques utilize individual RMB foils (or preformed pieces) or the RMB may be formed directly between the parts to be joined using suitable thin-film deposition processes. In other embodiments the parts functionally couple by other techniques such as, for example, diffusion bonding techniques. Generally speaking, diffusion bonding involves holding components under load at elevated temperature in a protective atmosphere or vacuum. The loads used are typically lower than those that cause macrodeformation of the components. Bonding operations may be performed under vacuum or in an inert gas atmosphere, or, in some embodiments, in air. Diffusion bonding may also include the use of interlayers and the formation of a transient liquid phase thereof. Further, in some embodiments a eutectic joint can be formed. This is similar to other joining methods that include intimate contact and application of elevation temperature except the two materials that form the eutectic joint possess a lower melting point than either adjacent substrate. Further, a localized eutectic joint can be formed via applied laser energy since the temperature of the pieces themselves are not elevated to form the bond. In such embodiments the stresses (e.g. due to TCE mismatch) at service temperature are less. The localized heat may also be provided by patterned resistors on the substrate or by inductively coupled metal traces.

The green-sheet is typically a polymer-ceramic composite that is comprised of an organic (polymer) binder filled with glass, ceramic, or glass-ceramic or mixtures thereof. The organic binder may also contain plasticizers and dispersants. To form electrically conductive pathways, thick-film metal inks and pastes are used to form pre-cursor pathways that form electrically conducting pathways following co-firing. Thick-film pastes or inks may contain metal for formation of electrical pathways or dielectrics for formation of integrated passives such as resistors and capacitors. The organic vehicle may contain polymers, solvents and plasticizers. Thick-film technology is further described in J. D Provance, "Performance Review of Thick Film Materials", Insulation/Circuits, (April 1977), and in Morton L. Topfer, "Thick-film Microelectronics, Fabrication, Design, and Applications (1977), pp. 41–59, the contents of each of which are hereby incorporated by reference.

Thus, select embodiments of the MULTI-PATH, MONO-POLAR CO-FIRED HERMETIC ELECTRICAL FEEDTHROUGHS AND METHODS OF FABRICATION THEREFOR are disclosed. One skilled in the art will appreciate that the invention can be practiced with embodiments other than those disclosed. The disclosed embodiments are presented for purposes of illustration and not limitation, and the invention is limited only by the claims.

For example, an electrically neutral member can optionally be fabricated as part of the monolithic structure. For example, so that the electrically neutral member contacts with at least one of the layers. In one exemplary form of this aspect of the invention, said electrically neutral member can comprise a side-castellation member, a metallized via member, a metallized interlayer member or the like. In the case of a metallized interlayer member an optional electrical field shielding member can be located near the interlayer member so that undesirable capacitive or other electrical effects are avoided. Thus, one or more electrically neutral members can be used to promote thermal transfer, for instance, as a heat sink to dissipate high temperatures that can be encountered during high voltage therapy delivery (e.g., defibrillation therapy) or other high energy applications. Furthermore, one or more electrically neutral members can add structural integrity to the monolithic member (e.g., between adjacent layers, at the periphery, etc.).

In an additional form of the invention, the relative impedances, dimensions, sizes, or volumes of a current- or signal-carrying pathway—whether composed of a single- or multi-via structures—within a given layer or adjacent layer(s) can be adjusted to balance the distribution of the current or signal. Of course, the multi-path, mono-polar embodiments of the present invention can be fabricated as an array with diverse other electric interconnect structures (e.g., capacitive-filtered feedthroughs, single-path non-filtered feedthroughs, etc.) or can be combined after fabrication with such other structures as the need arises.

We claim:

1. A mono-polar, multi-conductive path miniaturized hermetic electrical interconnect for an implantable medical device (IMD), comprising:
    a monolithic structure derived from at least three discrete dielectric layers wherein each one of said layers includes at least one aperture filled at least partially with a conductive material, and wherein at least one of said layers includes at least one additional aperture also filled at least partially with a conductive material; and
    at least one conductive interlayer disposed between an adjacent pair of ceramic layers and electrically coupling the at least a pair of apertures together, wherein one of the adjacent pair of layers comprises said at least one of said layers.

2. A mono-polar, multi-conductive path miniaturized hermetic electrical interconnect according to claim 1, wherein each of said at least three discrete dielectric layers includes at least three apertures filled at least partially with a conductive material.

3. A mono-polar, multi-conductive path miniaturized hermetic electrical interconnect according to claim 2, wherein the at least three apertures of adjacent layers are radially offset from each other.

4. A mono-polar, multi-conductive path miniaturized hermetic electrical interconnect according to claim 3, wherein the radial offset comprises a substantially equivalent offset distance for each of the adjacent layers.

5. A mono-polar, multi-conductive path miniaturized hermetic electrical interconnect according to claim 1, wherein said at least one conductive interlayer is disposed between adjacent layers of the at least three discrete dielectric layers.

6. A mono-polar, multi-conductive path miniaturized hermetic electrical interconnect according to claim 5, further comprising a conductive surface pad providing electrical communication to the at least one of the apertures.

7. A mono-polar, multi-conductive path miniaturized hermetic electrical interconnect according to claim 1, wherein the dielectric material comprises one of: $Al_2O_3$ material, a $Al_2O_3$—$ZrO_2$ material, $ZrO_2$, a glass material.

8. A mono-polar, multi-conductive path miniaturized hermetic electrical interconnect according to claim 7, wherein the glass contains at least one of: a $SiO_2$ material, a boron material, a Group II oxide.

9. A mono-polar, multi-conductive path miniaturized hermetic electrical interconnect according to claim 1, wherein the conductive material comprises one of at least one of the following materials: a platinum material, a platinum-gold alloy material, a platinum-iridium material, a platinum alloy material, a tungsten material, a tungsten-molybdenum material, a niobium material, a silver material, a gold material, a silver-palladium material, a gold-palladium material.

10. A mono-polar, multi-conductive path miniaturized hermetic electrical interconnect according to claim 1, wherein the IMD comprises one of: a pacemaker, a drug pump, a cardioverter-defibrillator, an implantable nerve stimulator, a medical electrical lead, a primary battery, a secondary battery, a capacitor, an implantable pulse generator, a data logging device, an implantable physiologic sensor.

11. A mono-polar, multi-conductive path miniaturized hermetic electrical interconnect according to claim 1, wherein at least one layer of the at least three discrete ceramic green-sheet layers comprises a low temperature co-fire ceramic (LTCC) material.

12. A mono-polar, multi-conductive path miniaturized hermetic electrical interconnect according to claim 11, wherein the LTCC material has a melting point between about 850 degrees Celsius and 1150 degrees Celsius.

13. A mono-polar, multi-conductive path miniaturized hermetic electrical interconnect according to claim 1, wherein at least one layer of the at least three discrete ceramic green-sheet layers comprises a high temperature co-fire ceramic (HTCC) material.

14. A mono-polar, multi-conductive path miniaturized hermetic electrical interconnect according to claim 13, wherein the HTCC material has a melting point between about 1100 degrees Celsius and 1700 degrees Celsius.

15. A mono-polar, multi-conductive path miniaturized hermetic electrical interconnect according to claim 1, wherein the at least one aperture and the at least one additional aperture comprise one of different dimensions and different volumetric capacity.

16. A mono-polar, multi-conductive path miniaturized hermetic electrical interconnect according to claim 1, further comprising an electrically neutral member in contact with at least one of the layers, wherein said electrically neutral member consists of:
    a side-castellation member,
    a metallized via member,
    a metallized interlayer member, wherein the metallized interlayer member further comprises an electrical field shielding member located near the metallized interlayer member.

17. A mono-polar, multi-conductive path miniaturized hermetic electrical interconnect according to claim 16, wherein the electrical termination pad is applied following a high-temperature co-firing of the electrical interconnect using a post-fire thick-film metallization process.

18. An electrical interconnect according to claim 17, wherein said metallization is selected from a group consisting of a gold material, a platinum material, a platinum alloy material, a platinum-gold material, a platinum-iridium material, a niobium material, a niobium alloy material, a tantalum material, a tantalum alloy material, a glass-ceramic material.

19. A process for fabricating a mono-polar, multi-conductive path miniaturized hermetic electrical interconnect for an implantable medical device (IMD), comprising:
   forming at least one aperture through opposing major surfaces of each of at least three ceramic green-sheet layers;
   forming at least one additional aperture through opposing major surfaces of at least one of said three ceramic green-sheet layers;
   depositing a conductive paste to at least partially fill a portion of each aperture of the at least three discrete layers;
   depositing a conductive interlayer material between adjacent layers in a configuration capable of forming an electrically common electrical pathway utilizing the apertures, wherein said common electrical pathway extends through opposing major surfaces of each of the at least three layers;
   aligning the at least three layers; and
   sintering the aligned layers, the conductive paste, and the conductive interlayer material together at about between 600 degrees Celsius and 1,600 degrees Celsius to form a monolithic hermetic feedthrough structure.

20. A method according to claim 19, wherein the IMD comprises one of: a pacemaker, a neurological stimulator, a drug pump, a cardioverter-defibrillator, a deep brain stimulator, a medical electrical lead, a primary battery, a secondary batter, a capacitor, a physiologic sensor.

* * * * *